United States Patent [19]
Ahs

[11] 3,938,614
[45] Feb. 17, 1976

[54] CUSHION MEMBER FOR SOUND-PROOF SEALING

[75] Inventor: Inge Wilgot Ahs, Koppom, Sweden

[73] Assignee: Aktiebolaget Lennartsfors Mekaniska Verkstad, Lennartsfors, Arjang, Sweden

[22] Filed: June 20, 1973

[21] Appl. No.: 371,650

[30] Foreign Application Priority Data
June 20, 1972 Sweden.............................. 8110/72

[52] U.S. Cl. .................... 181/129; 2/209; 128/151; 179/182 R; 181/33 R
[51] Int. Cl.² ...................... H04R 25/00; H04R 1/10
[58] Field of Search .......... 181/33 R, 33 G, 33 GB, 181/33 K, 23, 129; 179/182 R; 2/209; 128/151, 152

[56] References Cited
UNITED STATES PATENTS

| | | |
|---|---|---|
| 2,621,751 | 12/1952 | Kettler................................. 181/23 |
| 2,850,012 | 9/1958 | Becker................................ 128/152 |
| 2,989,598 | 6/1961 | Touger et al..................... 179/182 R |
| 2,990,553 | 7/1961 | Ulrich et al............................ 2/209 |

Primary Examiner—Stephen J. Tomsky
Attorney, Agent, or Firm—Fred Philpitt

[57] ABSTRACT

A cushion member for sound-insulating and air-tight sealing, which cushion is to be attached substantially along the edge of a first surface, which at this edge is connected via the cushion with another surface, which need not have a form absolutely conforming to the first surface at the connecting surface and need not be smooth. The cushion consists of an elongated casing filled with balls of plastic material and with a cylindrical cross-section of soft, flexible and air-impervious material and it is adapted to be attached to the first surface.

10 Claims, 7 Drawing Figures

CUSHION MEMBER FOR SOUND-PROOF SEALING

The present invention relates to a cushion member for sound-insulating and air-tight sealing, which cushion is adapted to be attached substantially along the edge of a first surface, which at this edge is connected via the cushion with another surface, which need not have a form absolutely conforming to the first surface at the connecting surface and need not be smooth. The cushion member is especially intended for use with substantially cup-shaped ear-protecting means or earphones for sound-proof sealing between the edge of these means and the skin around the ears. The cushion member can also to be attached to the edge of a cover of the outer casing of some strongly noisy apparatus, such as a compressor etc., or around doors or windows for preventing sounds from outside penetrating into apartments, etc. In the latter case the cushion member according to the invention has also an exceedingly good effect against air drafts.

Polyurethane foam surrounded with a welded plastic foil casing or plastic cushions filled with a liquid have previously been used as ear-protectors. The cushions filled with liquid have provided the best sealing, but they are relatively heavy, and there is also a risk that the casing will break and the liquid run out, which is not especially comfortable to the wearer of the ear-protector. As to the firstmentioned cushion, no good contact to the skull is obtained, and especially not if the wearer has an irregular head shape or wears glasses. The above-mentioned disadvantages are especially striking at low frequencies, within which frequency range noise is typically present.

The above-mentioned disadvantages are eliminated to a large extent by my cushion member wherein the cushion consists of an elongated casing filled with balls of plastic or a similar material the casing having a cylindrical cross-section and consisting of a soft, flexible and air-impervious material. The cushion member is adapted to be attached to a first surface.

The balls that are filled into the casing, which casing preferably consists of sewed or welded plastic fabric, can be either hollow or solid or porous. The surface of each of the balls is preferably hard and smooth so that the balls can slide easily against each other, but the balls can also be made of a soft material, which means in that they will be somewhat deformed in addition to being displaced relative to each other. The size of the balls can vary within wide limits depending on the intended field of application of the cushion member, although a diameter of the balls in the order of 2 mm has been found to be most practical. All the balls need not be the same size, although this is preferred.

When using the cushion member as a sound-proof seal between the cover and the casing of a compressor, or around doors and windows, the casing is preferably rather elongated and provided on one of its longitudinal sides with either a double-adhering tape, or with a magnet edging in case the cushion is to be attached to on a magnetizable material.

The casing can also be divided into compartments, in which the balls are placed, which means that the balls are more easily kept in the desired locations and the formation of undesired cavities avoided. This is especially worthwhile when the cushion member is to be used for a long period of time.

The greatest advantage of the cushion member according to my invention is that it adapts itself very easily to the form of the underlying surface so that the surfaces to which it makes contact can be very rough and have relatively large projecting portions without this influencing the sound-insulating properties of the cushion. The cushion member is also very light by virtue of its being filled with hollow balls or with solid balls of a light material, which is especially important in ear-protectors and headphones. This property also has the effect that it does not feel as if it sticks to the skin, which is the case with liquid-filled cushions, in spite of the good contact with the skin. People with very different head shapes and even people with glasses can use the cushion member according to the invention, which cases have previously given very great problems, especially in cushions filled with polyurethane foam.

In order that the cushion member remain as hygienic as possible when using ear-protectors or earphones it is adapted to be detachably attached and in fact may be of a kind that is used only once. This is achieved by providing it with one or more outwardly extending parts, by which it can be easily attached and removed from an ear-protector or an earphone. This is best achieved when the casing extends substantially in the form of a cylinder from the outer periphery of the cushion member and terminates at its outer edge with a rubber band (or contracting device with a similar effect) so that the cushion can be attached to the ear-protector or the earphone, by fitting the cylinder-shaped part around the ear-protector, after which it is retained by the action of the contracting device.

The invention is described more in detail below with reference to the enclosed drawings where FIG. 1 is a section through a cup-shaped ear-protector with an embodiment of a cushion member according to the invention, FIG. 2 is a view from below of the same ear-protector as FIG. 1, FIG. 3 shows schematically a device, by means of which the efficiency of the cushion member has been tested in practice, FIG. 4 shows results between a cushion member according to the invention and a cushion filled with polyurethane foam obtained with the device according to FIG. 3, and FIG. 5 shows a cross-section through a detail of a cushion member according to the invention mounted between cover and outer casing of e.g. a compressor aggregate.

Figure 1:
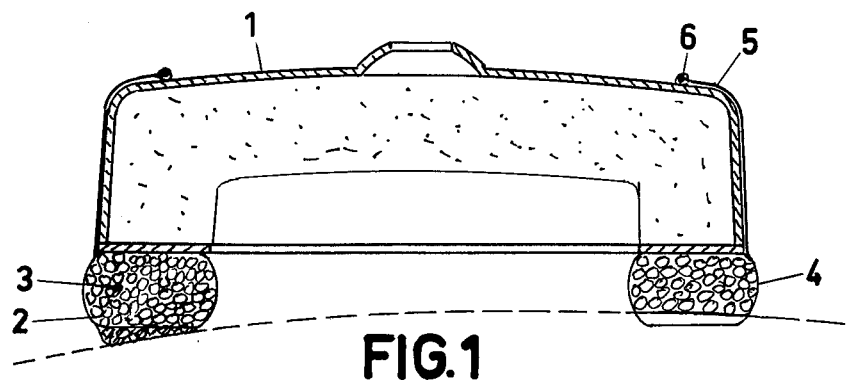
Figure 2:
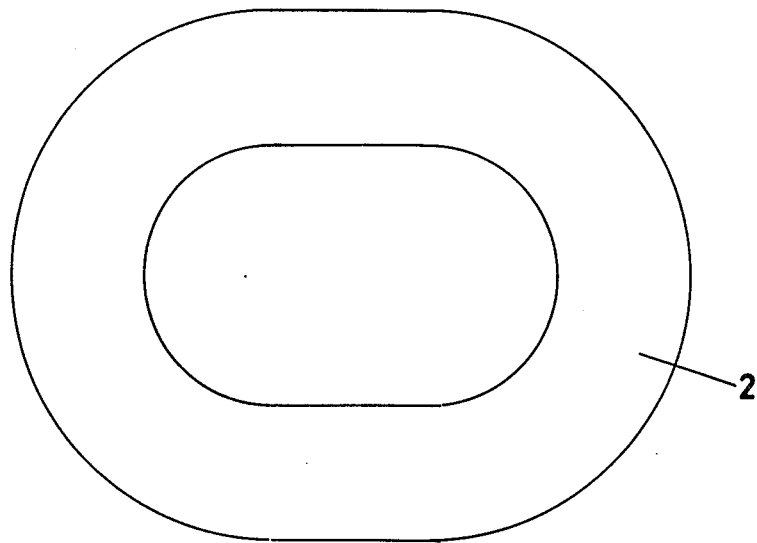

FIG. 1 is a sectional view through a cup-shaped ear-protector 1 of standard type, on whose edge an embodiment of a cushion member 2 according to my invention is attached. The cushion consists of a ring having substantially the same outer diameter as the earphone or ear-protector and consisting of hollow, welded or sewed plastic fabric 4, in which balls 3 are filled, being either solid or hollow. The plastic fabric continues in the form of a cylinder 5 upwards from the outer periphery of the ring and is terminated with a rubber band 6 at its outer edge, by which rubber band the cushion member 2 is kept in position. Alternatively, 6 can be a tape with adhesive on both sides. Thus the cushion member is very hygienic, as each user of ear-protectors can have his own cushion member. The cushion member can also be made in a so-called disposable embodiment and is then thrown away after use. A great advantage of the cushion member is also that it suits substantially all current types of cup-shaped ear-protectors and earphones. FIG. 2 is a view from below of the cushion member, the annular shape of the cushion here appearing especially clearly.

Figure 3:
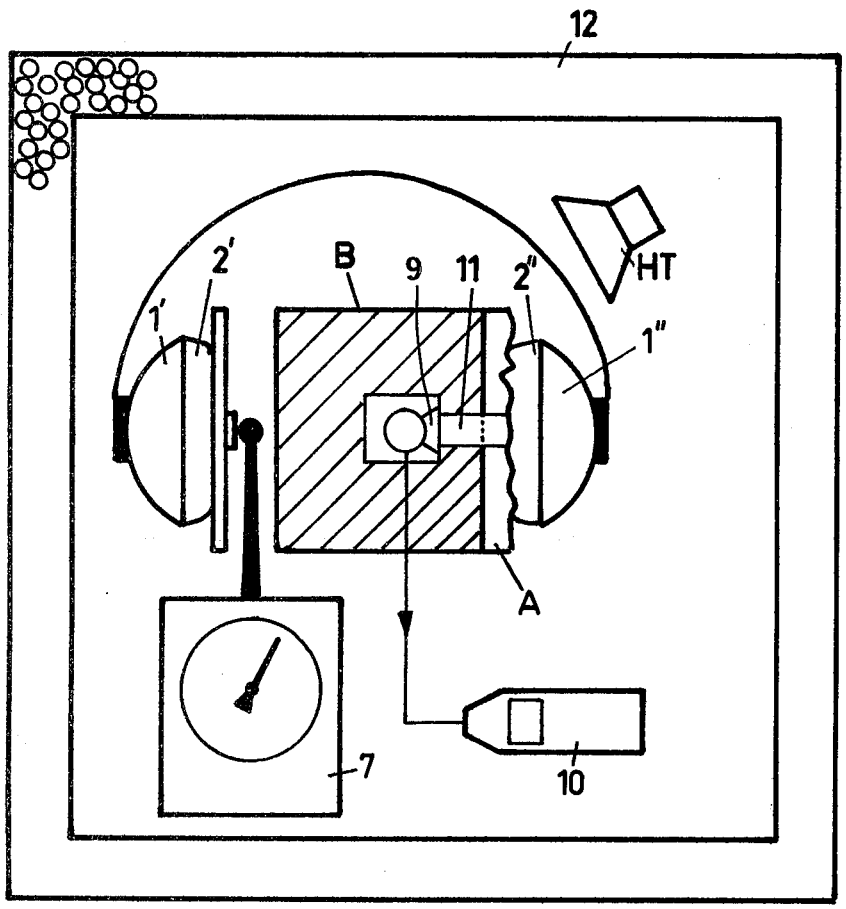

FIG. 3 is a schematical view of a device by means of which the efficiency of the cushion member has been tested in practice. An ear-protector with two ear casings 1' and 1'' with adapted cushion member 2' and 2'', respectively, is placed so that one ear casing 1'' with the cushion member 2'' is adapted to an annular contact medium A at a certain pressure produced by a spring balance 7 acting on the other ear casing 1' and its force then propagating via the loop 8 to the first ear casing 1''.

The contact medium A is replaceable to simulate different conditions, e.g. a skull with or without glasses and different shapes of the jaw-bone. The medium A is adapted on a sound-proof casing B, in whose interior a measuring microphone 9 is present, whose signal is fed onto a dB-measuring means 10. A channel 11 leads into the measuring microphone 9 in the casing 10 and debouches into the intermediate hole of the contact medium A. A loud-speaker HT emits a sound signal composed of several frequencies with an octave between adjacent frequencies, so that the efficiency of the cushion member can be found by means of the measuring microphone at different frequencies and at different sound intensities. The whole measuring device is enclosed in a sound-insulated cabinet 12 in order that the measuring result should not be distorted by other sound signals than those intended.

Figure 4:
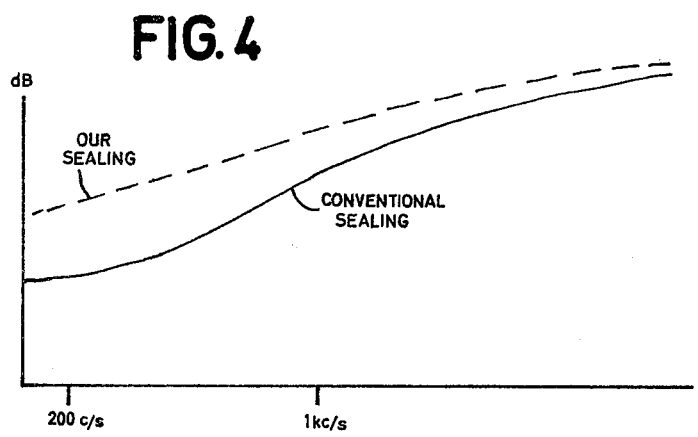

At tests carried out with the above-mentioned device the cushion member according to the invention with solid balls and a cushion member of previously general type with polyurethane foam in a plastic foil casing have been tested with six different types of contact media A under identically the same conditions, and FIG. 4 shows a diagram of the sound attenuation in dB let through as a function of the frequency of a cushion member according to the invention with a dashed line and the previously generally used cushion member with a continuous line. The curves show average curves obtained for the different contact media A. In general it can be said that the lower attenuation obtained for the lower frequencies of the two cushion members depends on the attenuation material included in the casings and to a higher degree on the "leakage" obtained at the sealing against the skull, which latter condition the cushion member according to the invention is to eliminate. At the dashed curve (the cushion member according to the invention) the permeability is less, which is mainly due to the better adhesion to the support of the cushion member according to the invention.

It should be pointed out once more that the two curves are average ones and show mainly the tendency to better attenuation at low frequencies of the cushion member according to the invention. The more projecting parts the contact media had, the better was the performance of the cushion member according to the invention relative to that of the cushion previously used.

Figure 5:
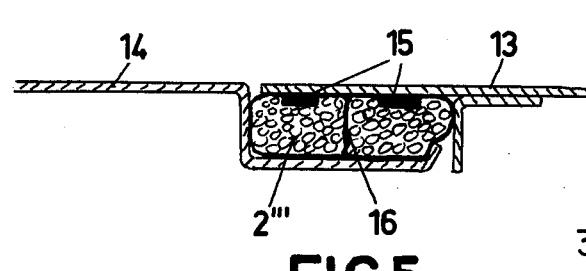

FIG. 5 is a cross-sectional view of a detail of a cushion member 2''' according to my invention attached to a cover 13 and making contact with the outer casing 14 of e.g. a compressor aggregate. The cushion is here provided with a magnet edging 15 on its side facing the cover, by means of which it is attached to the iron cover. The cover 13 and the outer casing 14 of the aggregate are in known manner provided with a medium for a sound-proof sealing on the inside, but the very sound-proof sealing between cover and casing has previously offered great problems, because it is difficult to have the cover seal tightly at the outer casing, especially at frequent use of the aggregate. These problems have now been solved in a simple and cheap manner according to the invention. The cushion member is here preferably divided into compartments, by an intermediate wall 16, so that the balls will not collect in only one place and leave another place empty.

Figure 6:
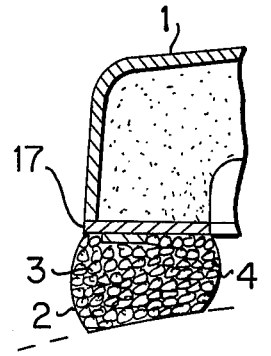
FIG. 6 shows a partial section of the ear-protector of FIG. 1 having an annular magnet attached to the cushion as the holding means.

FIG. 6 is a cross-sectional view of a portion of the ear-protector of FIG. 1 including the cushion member 2 containing balls 3 having an annular magnet 17 attached to cover 4 to hold the cushion member on a metallic ear-protector.

Figure 7:
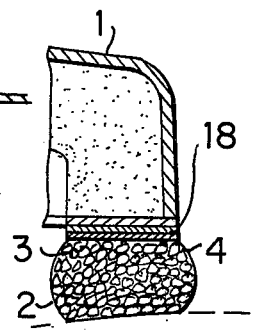
FIG. 7 shows a partial section of the ear-protector of FIG. 1 having an annular double-adhering tape attached to the cushion as the holding means.

FIG. 7 is a cross-sectional view of a portion of the ear-protector of FIG. 1 including the cushion member 2 containing balls 3 and having an annular, detachable, double-adhesive tape 18 attached to cover 4 to hold the cushion member on the ear-protector.

Moreover, the cushion member according to my invention can be adapted as a sealing around windows and doors, where it does not only provide good sealing against noise, which in our noisy age is absolutely necessary, but also provides excellent sealing against air drafts, a good combination effect being obtained.

What we claim is:

1. In a cup-shaped, ear-covering device having an annular flange adapted to contact the head of the wearer around the ear, the improvement comprising a sound-barrier structure including an annular, hollow casing having a generally-cylindrical cross-section in an unsqueezed condition, formed of a soft, pliable material and shaped to fit against said annular flange between said annular flange and said head of said wearer, a plurality of freely-moveable, small balls disposed in the interior of said casing, whereby said structure deforms and conforms to the surface of said annular flange and said head of said wearer when said structure is squeezed against said head of said wearer by said ear-covering device, and holding means for detachably holding said structure against said ear-covering device.

2. A device in accordance with claim 1 wherein the concentration of the balls within the casing is less than a concentration sufficient to fill the total void space within said casing.

3. A device in accordance with claim 1 wherein the ear-covering device is metallic and the holding means is a magnetic means mounted on the side of the casing which is against the annular flange.

4. A device in accordance with claim 1 wherein the holding means is detachable, double-adhering adhesive tape means mounted on the side of the casing which is against the annular flange.

5. A device in accordance with claim 1 wherein the holding means is an elastic means attached to the casing and extending about the periphery of the ear-covering device and rearwardly from said casing toward the rearward portion of said ear-covering device.

6. A device in accordance with claim 5 wherein the elastic means includes a pliable connecting piece attached to the casing, extending rearwardly from said casing toward the rearward portion of said ear-covering device and terminating in an annular, elastic, free edge smaller than the maximum periphery of said ear-covering device.

7. A device in accordance with claim 1 wherein the balls are made of hard plastic having a smooth surface to facilitate the free movement of said balls against one another.

8. A device in accordance with claim 1 wherein the balls are all of substantially the same size.

9. A device in accordance with claim 1 wherein the balls have an average diameter in the range of about 1.5 to 5.0 mm.

10. A device in accordance with claim 1 wherein the casing material is inelastic.

* * * * *